US011680224B2

(12) United States Patent
Cermak et al.

(10) Patent No.: US 11,680,224 B2
(45) Date of Patent: Jun. 20, 2023

(54) HYDROXY FATTY ACID SYNTHESIS

(71) Applicant: The United States of America, as Represented by the Secretary of Agriculture, Washington, DC (US)

(72) Inventors: Steven C Cermak, Galesburg, IL (US); Terry Isbell, Elmwood, IL (US); Benjamin A Lowery, Princeville, IL (US)

(73) Assignee: The United States of America, as represented by The Secratery of Agriculture, Washington, DC (US)

( * ) Notice: Subject to any disclaimer, the term of this patent is extended or adjusted under 35 U.S.C. 154(b) by 0 days.

(21) Appl. No.: 17/519,162

(22) Filed: Nov. 4, 2021

(65) Prior Publication Data
US 2022/0135902 A1    May 5, 2022

Related U.S. Application Data

(60) Provisional application No. 63/109,701, filed on Nov. 4, 2020.

(51) Int. Cl.
*C11C 3/12* (2006.01)
*C07D 303/42* (2006.01)

(52) U.S. Cl.
CPC ............ *C11C 3/126* (2013.01); *C07D 303/42* (2013.01)

(58) Field of Classification Search
CPC ......... C11C 3/12; C11C 3/126; C07D 303/42; C07C 67/31
See application file for complete search history.

(56) References Cited

U.S. PATENT DOCUMENTS

| 3,778,465 | A | * | 12/1973 | Barnstorf | C07D 303/42 560/189 |
| 4,171,420 | A | * | 10/1979 | Doorakian | C08G 59/688 525/507 |
| 4,825,004 | A | * | 4/1989 | Rutzen | C07C 29/149 568/864 |
| 6,274,750 | B1 | * | 8/2001 | Sato | C09D 11/102 530/211 |
| 6,583,302 | B1 | * | 6/2003 | Erhan | C10M 105/42 554/149 |
| 2006/0264568 | A1 | * | 11/2006 | Pajerski | C08G 18/0823 525/453 |
| 2008/0154053 | A1 | * | 6/2008 | Erhan | C07C 67/26 554/213 |

FOREIGN PATENT DOCUMENTS

| CN | 103695183 | * | 4/2014 | ............... C11C 1/02 |
| KR | 20200038715 | * | 4/2020 | ............ C08G 18/36 |

OTHER PUBLICATIONS

CN103695183, Beijing University of Agriculture, Method for preparing hydroxy fatty acids by utilizing swill-cooked dirty oil, English translation, 1 page abstract (Year: 2014).*

(Continued)

*Primary Examiner* — Yate' K Cutliff
(74) *Attorney, Agent, or Firm* — John D. Fado; Maria Restrepo-Hartwig (57) ABSTRACT

The invention relates to methods for the synthesis of hydroxy fatty acids from unsaturated fatty acids via epoxidation and catalytic hydrogenation.

18 Claims, 6 Drawing Sheets

(56) References Cited

OTHER PUBLICATIONS

KR20200038715, Nat. Univ Chungbuk Ind ACAD COOP Fond, A method for the synthesis of bio-based polyurethanes using hydroxy fatty acids produced by microbial conversion of vegetable oils, English translation, 1 page abstract (Year: 2020).*
Pages—XATART-PARES, Xavier, et al., Synthesis of new derivatives from vegetable oil methyl esters via epoxidation and oxirane opening, Recent Developments in Synthesis of Fatty Acid Derivatives, Ed. Knothe, et al., AOCS Press, 18 pages (include 141-156) (Year: 1999).*
Campanella, A., et al., Degradatin of the oxirane ring of epoxidized vegetable oils in lliquid-liquid systems: II. Reactivity with solvated acetic and peracetic acids, Latin American Applied Research, vol. 35, No. 3, pp. 211-215 (Year: 2005).*

* cited by examiner

HYDROXY FATTY ACID SYNTHESIS

FIELD OF THE INVENTION

The invention relates to methods for the synthesis of hydroxy fatty acids from epoxidized fatty acids, and the synthesis of the epoxidized fatty acids from unsaturated fatty acids.

BACKGROUND OF THE INVENTION

Hydroxy fatty acids are a major industrial chemical used in lubricants, greases, cosmetics, and as raw material for the production of nylon. Currently hydroxy fatty acids are nearly completely supplied by castor oil which is grown mostly in India, China, and Brazil. The production of castor oil is fraught with many agronomic problems along with significant well documented human health hazards. These problems make the prospect of growing castor seeds as a domestic source of hydroxy fatty acid in the U.S. unrealistic.

A long-term effort over the last four decades to introduce lesquerella as a domestic source of hydroxy fatty acids to supplement or replace castor oil imports has failed to reach commercial production. This shortcoming appears to be from the aversion to the risk associated with the initial establishment of a new crop, rather than lesquerella's agronomic performance.

Epoxidation of fats and oils is a historically well-known process that has been used commercially to produce the commodity epoxidized oils at low cost where the epoxidized oil is used in coatings and adhesives. Hydrogenation of fats and oils has been conducted commercially for a very long time to produce food grade oils for margarines and many other applications at very low cost (less than US$0.05 per pound). The challenge for hydrogenation in the presence of a hydroxy fatty acid is the side-product dehydrogenation that occurs on the fatty acid to form a ketone. Hydrogenation of both, castor and lesquerella oils, at atmospheric pressure and high temperatures have been reported. In these cases, formation of ketone was minimized while hydrogenation of the olefin was successful.

Metal hydride reductions of epoxides, typically using sodium borohydride or lithium aluminum hydride, using stochiometric amounts of the hydrides are known. These methods are not especially suitable for industrial scale production of materials because they use equal molar ratios of the reagents. While there are reports of catalytic reduction of epoxides, these are nearly all associated with small aromatic molecules with terminal epoxides which can act as stabilizing functionality during the reaction.

Catalytic hydrogenation of epoxidized soybean oil with a Raney nickel catalyst has been reported to have reduced the epoxides to a poly hydroxide compound. Based only on a hydroxyl value titration, the yield for the reduction was in the mid 90% range, however, no spectroscopic support of the structures was provided. Mack and Bickford (Mack, C. H., and W. G. Bickford, 1953, "Hydroxystearic Acids. I. The Catalytic Hydrogenation Of The 9,10-Epoxystearates," J. Org. Chem. 18(6): 686-692.) reported that the Catalytic hydrogenation of methyl 9,10-epoxystearate or 9,10-epoxystearic acid in glacial acetic acid as the solvent and Pd/C at 1 mole % under 2 atmospheres of hydrogen at room temperature has been reported to provide good yields of only 10-hydroxy stearic acid or methyl 10-hydroxy stearate (Mack, C. H., and W. G. Bickford, 1953, "Hydroxystearic Acids. I. The Catalytic Hydrogenation Of The 9,10-Epoxystearates," J. Org. Chem. 18(6): 686-692). However, a eutectic melting point study of mixtures of 9-hydroxy and 10-hydroxy stearates demonstrated that the Mack and Bickford method produced an equal mixture of the 9 and 10 positional isomers from the hydrogenation reaction (Cochrane C. C. and Harwood H. J., 1961, "Phase properties of mixtures of 9- and 10-oxo-octadecanoic acids and of 9- and 10-hydroxyoctadecanoic Acids," J. Org. Chem. 26:1278-1282). The difficulty of the removal of the acetic acid probably hindered the Mack and Bickford hydrogenation method from commercial adoption.

Therefore, new methods for the synthesis of hydroxy fatty acids from readily available oils, at a cost below that of current castor oil import price are needed.

SUMMARY OF THE INVENTION

Provided herein is a method for the synthesis of hydroxy fatty acids from mono- and poly-unsaturated fats via a two-step process. The process involves peracid epoxidation of the unsaturated fat followed by catalytic hydrogenation using a palladium catalyst in the presence of a catalytic amount of an organic acid. The method results in good yields of hydroxy fatty acids with minimal formation of ketone by-products.

In an embodiment, the invention relates to a method for the synthesis of at least one hydroxy fatty acid by reacting in a pressurized container at least one epoxidized fatty acid in a solvent, with an organic acid and a catalyst. The method optionally comprises reacting an unsaturated fat with formic acid and hydrogen peroxide to obtain the epoxidized fatty acid. In some embodiments of the invention, the epoxidized fatty acid is obtained from soybeans, sunflower, safflower, tallow, pennycress, *crambe*, rapeseed, *Brassica carinata*, meadowfoam, coriander, soybean, camelina, or jojoba. In some embodiments of the invention, the organic acid is acetic acid, oxalic acid, trifluoroacetic acid, trichloroacetic acid, or tribromoacetic acid. In some embodiments of the invention, the organic acid is oxalic acid.

In an embodiment, the invention relates to a method for the synthesis of at least one hydroxy fatty acid from at least one epoxidized fatty acid in a solvent, in the presence of an organic acid and a catalyst, where the catalyst is palladium on carbon or platinum on carbon. In some embodiments of the invention, in the method for method for the synthesis of at least one hydroxy fatty acid from at least one epoxidized fatty acid, the catalyst in the method for the synthesis of at least one hydroxy fatty acid from at least one epoxidized fatty acids is palladium on carbon. In some embodiments of the invention, 1 equivalent of the epoxidized fatty acid is reacted with from about 0.0020 equivalents of palladium to about 0.021 equivalents of palladium. In some embodiments of the invention, 1 equivalent of epoxidized fatty acid is reacted with about 0.0030 equivalents of palladium.

In an embodiment, the invention relates to a method for the synthesis of at least one hydroxy fatty acid from at least one epoxidized fatty acid in a solvent, in the presence of an organic acid and a catalyst, where the method is performed under pressure. In some embodiments of the invention, the pressure of the method for the synthesis of at least one hydroxy fatty acid from at least one epoxidized fatty acid is at least about 14 psi to at least about 1100 psi. In some embodiments of the invention, the pressure of the method for the synthesis of at least one hydroxy fatty acid from at least one epoxidized fatty acid is at least about 160 psi to at least about 1000 psi.

In an embodiment, the invention relates to a method for the synthesis of at least one hydroxy fatty acid from at least one epoxidized fatty acid in a solvent in the presence of an organic acid and a catalyst, where the method produces at least one hydroxy fatty acid and at least one ketone fatty acid. In some embodiments of the invention, in the method for the synthesis of at least one hydroxy fatty acid from at least one epoxidized fatty acid the amount of ketone fatty acid produced is less than about 18% ketone fatty acid.

In some embodiments, the invention relates to the method for the synthesis of at least one hydroxy fatty acid from at least one epoxidized fatty acid, where the method further comprises obtaining the epoxidized fatty acid by reacting an unsaturated fat with formic acid and hydrogen peroxide.

In some embodiments of the invention, in the method for the synthesis of at least one hydroxy fatty acid from at least one epoxidized fatty acid, the solvent is not n-butyl propionate containing 1% sulfuric acid; ethanol; petroleum ether containing 1% acetic acid; anhydrous propionic acid; or glacial acetic acid. In some embodiments of the invention, the solvent in the method for the synthesis of at least one hydroxy fatty acid from at least one epoxidized fatty acid is ethyl acetate. In some embodiments of the invention, the synthesis of at least one hydroxy fatty acid from at least one epoxidized fatty acid is performed in an inert atmosphere. In some embodiments of the invention, the at least one epoxidized fatty acid used in the method for the synthesis of at least one hydroxy fatty acid has more than 7 carbons. In some embodiments of the invention, the temperature in the method for the synthesis of at least one hydroxy fatty acid from at least one epoxidized fatty acid is from about 20° C. to about 180° C. In some embodiments of the invention, the temperature in the method for the synthesis of at least one hydroxy fatty acid from at least one epoxidized fatty acid is about 50° C. In some embodiments of the invention, no acetate esters are synthesized in the method for the synthesis of at least one hydroxy fatty acid from at least one epoxidized fatty acid.

In an embodiment, the invention relates to a method for the synthesis of at least one hydroxy fatty acid from at least one epoxidized fatty acid, where the at least one epoxidized fatty acid is epoxidized methyl oleate, and the hydroxy fatty acid obtained is a 50:50 mixture of methyl 9-hydroxystearate and methyl 10-hydroxystearate.

BRIEF DESCRIPTION OF THE DRAWINGS

FIG. 3A to 3C depict methyl oleate reaction schemes.

DETAILED DESCRIPTION

The present invention relates to the synthesis of hydroxy fatty acids from unsaturated fats via a two-step process.

The inventors have devised a method for obtaining a hydroxy fatty acid source via a chemical route, below the current cost of castor oil import prices. The method may utilize existing readily available commodity oilseed crops such as sunflower, canola, soybean, safflower, tallow, pennycress, crambe, rapeseed, Brassica carinata, meadowfoam, coriander, camelina, or jojoba. The synthetic chemistry is performed through coupling of two proven chemical reactions of epoxidation and catalytic hydrogenation to yield monohydroxy fatty acids at the site of the original olefin positions.

The inventors epoxidized methyl oleate to 9,10-epoxy stearate using a peracetic hydrogen peroxide epoxidation method (Findlay et al. 1945) and this epoxide was used as the starting material for all subsequent hydrogenation reactions. The inventors surprisingly have found that epoxy methyl stearate can be rapidly reduced to mono-hydroxy esters by hydrogen over a Pd/C catalyst, when a catalytic amount of an acid co-catalyst is employed. The optimum condition for reduction of the epoxide was found to be at 50° C. with 1.0 mole % oxalic acid, and 0.3 mole % Pd/C with 160 psi hydrogen pressure. Increasing the acid co-catalyst concentration increased the rate of saturate side-product formation but did not increase the rate of reduction of the epoxide to hydroxide. Changing the Pd/C catalyst concentration had no impact on the rate of reaction. Increasing the temperature increased the rate of hydrogenation, but at the expense of also increasing the formation of saturates. After catalytic hydrogenation, the crude hydroxide reaction product containing ketones was further enriched in hydroxy concentration by reducing the ketone with $NaBH_4$ in an equal molar amount to the ketones present in the mixture. This yielded a final product with hydroxy content greater than 92%.

In an embodiment, the invention relates to a method for the synthesis of at least one hydroxy fatty acid, the method comprising reacting in a pressurized container at least one epoxidized fatty acid in a solvent, an organic acid, and a catalyst to obtain at least one hydroxy fatty acid. In some embodiments of the invention, the process for the preparation of hydroxy fatty acids from epoxidized fatty acids may be obtained from soybeans, sunflower, safflower, tallow, pennycress, crambe, rapeseed, Brassica carinata, meadowfoam, coriander, soybean, camelina, or jojoba.

Mack C. H. and Bickford W. G. (1953, supra) report the catalytic hydrogenation of methyl 9,10-epoxystearate or 9,10-epoxystearic acid in glacial acetic acid as the solvent and Pd/C at 1 mole % under 2 atmospheres of hydrogen at room temperature. In the reaction, Mack and Bickford use 0.0268 equivalents palladium for every one equivalent of epoxy stearate. While Mack and Bickford reported that the reaction yielded only 10-hydroxy stearic acid or methyl 10-hydroxy stearate. A eutectic melting point study of mixtures of 9-hydroxy and 10-hydroxy stearates demonstrated that the Mack and Bickford method produced an equal mixture of the 9 and 10 positional isomers from the hydrogenation reaction (Cochrane C. C. and Harwood H. J. 1961, supra).

Following method taught herein, a 50/50 mixture of 9-hydroxy and 10 hydroxy fatty acids is synthesized from an epoxidized fatty acid. Not wishing to be bound by any particular theory, it is believed that following the instant teachings, it is possible to obtain 50/50 hydroxy fatty mixtures from all epoxy fatty acids until the epoxide group gets close to the carboxylic acid functionality. At this point the distribution will start to favor one hydroxyl only. In some embodiments of the invention, the at least one epoxidized fatty acid used in the method for synthesizing at least one hydroxy fatty acid contains at least 7 carbons.

In an embodiment, the invention relates to a method comprising reacting in a pressurized container at least one epoxidized fatty acid in a solvent, an organic acid, and a catalyst to synthesize of at least one hydroxy fatty acid. In some embodiments of the invention, the organic acid used in the method of the invention is acetic acid, oxalic acid, trifluoroacetic acid, trichloroacetic acid, or tribromo acetic acid. In some embodiments of the invention, the organic acid used in the synthesis of at least one hydroxy fatty acid is oxalic acid.

In an embodiment, the invention relates to a method for synthesis of at least one hydroxy fatty acid from an epoxidized fatty acid in a solvent, in the presence of a catalyst. In an embodiment of the invention, the catalyst used in the synthesis of at least one hydroxy fatty acid is palladium on carbon or platinum on carbon. Palladium on carbon, often referred to as Pd/C, is a form of palladium used as a catalyst. In palladium on carbon the metal is supported on activated carbon in order to maximize its surface area and activity. Palladium on carbon is a palladium-based hydrogenation catalyst with numerous applications including organic chemistry, fuel cell technology, and the production of hydrogen via bioethanol reforming for alternative energy sources. Platinum on Carbon materials are powders composed of platinum on a matrix activated carbon support and are available with a variety of loading percentages. Platinum on carbon is catalyst material with applications in synthetic chemistry such as hydrogenation and hydrogenolysis of organic compounds, alternative energy, and fuel cell technologies. In some embodiments of the invention, in the method for the synthesis of at least one hydroxy fatty acid from an epoxidized fatty acid, the catalyst is palladium on carbon.

In an embodiment, the invention relates to a method for the synthesis of at least one hydroxy fatty acid from an epoxidized fatty acid, where 1 equivalent of the epoxidized fatty acid is reacted with from about 0.0030 equivalents of palladium to about 0.021 equivalents of palladium. In some embodiments of the invention, in the method for the synthesis of at least one hydroxy fatty acid from an epoxidized fatty acid, 1 equivalent of epoxidized fatty acid is reacted with about 0.0030 equivalents of palladium.

In an embodiment, the invention relates to a method for the synthesis of at least one hydroxy fatty acid from an epoxy fatty acid, where the synthesis is performed in a pressurized container. In some embodiments of the invention, the synthesis of at least one hydroxy fatty acid from an epoxy fatty acid is performed under a pressure that is at least about 14 psi to at least about 1100 psi. In some embodiments of the invention, the synthesis of at least one hydroxy fatty acid is performed under a pressure that is at least about 160 psi to at least about 1000 psi.

In an embodiment of the invention, the synthesis of at least one hydroxy fatty acid from an epoxy fatty acid produces at least one hydroxy fatty acid and at least one ketone fatty acid. In some embodiments, in the synthesis of at least one hydroxy fatty acid from an epoxy fatty acid the amount of ketone fatty acid produced is less than about 18% ketone fatty acid. In some embodiments of the invention, the amount of ketone produced in the synthesis of at least one hydroxy fatty acid from an epoxy fatty acid is less than about 15%; less than about 10%; less than about 9%; less than about 8%; less than about 7%; less than about 6%, less than about 5%, or a portion thereof.

In an embodiment, the invention relates to a method for the synthesis of at least one hydroxy fatty acid from an epoxy fatty acid where the method further comprises obtaining the epoxidized fatty acid by reacting an unsaturated fat with formic acid and hydrogen peroxide.

In an embodiment, reaction for the synthesis of at least one hydroxy fatty acid from an epoxy fatty acid is in a solvent. In an embodiment of the invention, the solvent is not n-butyl propionate containing 1% sulfuric acid; ethanol; petroleum ether containing 1% acetic acid; anhydrous propionic acid; or glacial acetic acid. In some embodiments of the invention, the solvent used in the method for the synthesis of at least one hydroxy fatty acid from an epoxy fatty acid is ethyl acetate.

In an embodiment, reactions of the invention are conducted under an inert gas atmosphere. As is well known to those of skill in the art, inert gas atmosphere may be any gas such as an anhydrous gas of $N_2$; Ar; He; or mixtures thereof. In an embodiment of the invention, synthesis of at least one hydroxy fatty acid from an epoxy fatty acid is performed at a temperature of from about 20° C. to about 180° C. In some embodiments of the invention, synthesis of at least one hydroxy fatty acid from an epoxy fatty acid is performed at a temperature of about 50° C.

In an embodiment of the invention, in the synthesis of at least one hydroxy fatty acid from an epoxy fatty acid no acetate esters are synthesized.

In an embodiment, the invention relates to the synthesis of at least one hydroxy fatty acid from an epoxidized fatty acid, where the epoxidized fatty acid is epoxidized methyl oleate, and where the hydroxy fatty acid obtained is a 50:50 mixture of methyl 9-hydroxystereate and methyl 10-hydroxystereate.

As used herein, the term "about" is defined as plus or minus ten percent of a recited value. For example, about 1.0 g means 0.9 g to 1.1 g.

The amounts, percentages and ranges disclosed herein are not meant to be limiting, and increments between the recited amounts, percentages, and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

The term "consisting essentially of" excludes additional method (or process) steps or composition components that substantially interfere with the intended activity of the method (or process) or composition. This term may be substituted for inclusive terms such as "comprising" or "including" to more narrowly define any of the disclosed embodiments or combinations/sub-combinations thereof. Furthermore, the exclusive term "consisting" is also understood to be substitutable for these inclusive terms.

"Optional" or "optionally" means that the subsequently described event or circumstance may or may not occur, and that the description includes instances in which said event or circumstance occurs and instances where it does not.

By the term "effective amount" of a compound or property as provided herein is meant such amount as is capable of performing the function of the compound or property for which an effective amount is expressed. As is pointed out herein, the exact amount required will vary from process to process, depending on recognized variables such as the compounds employed, and various internal and external conditions observed as would be interpreted by one of ordinary skill in the art. Thus, it is not possible to specify an exact "effective amount," though preferred ranges have been provided herein. An appropriate effective amount may be determined, however, by one of ordinary skill in the art using only routine experimentation.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

Embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby. All publications, patents, and patent applications mentioned in this specification are herein incorporated by reference to the same extent as if each individual publication, patent, or patent application was specifically and individually indicated to be incorporated by reference.

EXAMPLES

Having now generally described this invention, the same will be better understood by reference to certain specific examples, which are included herein only to further illustrate the invention and are not intended to limit the scope of the invention as defined by the claims.

Example 1

Materials Used

This example describes the materials used in the preparation of hydroxy fatty acids in the present invention.

Chemicals. Dibasic phosphate, methanol, hexanes, ethyl acetate, and hydrogen peroxide (30%) were purchased from Fisher Chemical Company; Fair Lawn, N.J., USA. Formic acid (98%) was purchased from Acros Organics; Mullica Hill, N.J., USA. Sulfuric acid (98%) was purchased from LabChem Inc.; Zelienople, Pa., USA. Oleic acid (technical grade), sodium chloride, sodium sulfate, hydrogen peroxide, formic acid, 10% palladium on carbon, sodium borohydride and acetic acid were purchased from Sigma-Aldrich Chemical company, St. Louis, Mo., USA.

Gas Chromatography (GC). Fatty acid analysis methods were used following Isbell T. A. and Kleiman R. (1994, "Characterization of Estolides Produced from the Acid-Catalyzed Condensation of Oleic Acid," J. Am. Oil Chem.' Soc. 71(4): 379-383) as described below. Fatty acid analyses were conducted on an Agilent Technologies (Santa Clara, Calif., USA) 6890N GC equipped with a flame-ionization detector and an auto sampler/injector. GC separations were obtained on a SBP-1 30 m×0.25 mm i.d. capillary column from Supelco (Bellefonte, Pa., USA). Fatty acid methyl esters (FAMEs) were separated using a programmed temperature ramp from 190° C. to 220° C. at 2° C./minute then 10° C./minute to 265° C. with a 10 minute hold at 265° C. Helium carrier gas flow rate was set to 1.4 mL/minute at 138 kPa, a septum purge of 4.0 mL/minute and a split ratio of 100:1. The injector and detector were maintained at 250° C. Saturated C8-C30 FAMEs provided standards for assigning peaks. A standard mix of C8-C30 saturated FAME GLC mixture supplied by Nu-Check Prep (Elysian, Minn., USA) which also contained 18:1, 18:2, 18:3, 20:1, and 22:1 was used to identify retention times of fatty ester components.

Nuclear Magnetic Resonance (NMR). $^1$H and $^{13}$C NMR experiments were recorded on a Bruker (Karlsruhe, Germany) Avance 500 spectrometer using a 5 mm broadband inverse (BBIO) probe with an absolute frequency of 500.11 MHz for $^1$H and 125.76 MHz for $^{13}$C. DEPT (distortionless enhancement by polarization transfer), COSY (correlated spectroscopy), HSQC (heteronuclear single quantum correlation), and HMBC (heteronuclear multiple bond correlation) two-dimensional spectra were also collected. Fifty milligrams of each sample were dissolved in 5 mL of 99.8% $CDCl_3$ (Cambridge Isotope Laboratories Inc., Andover, Mass., USA). Chemical shifts are expressed in ppm using the residual solvent peak as the internal standard. $^1$H experiments consisted of 16 scans, whereas 1024 scans were used in $^{13}$C experiments.

Acid value. Acid value was determined by AOCS method Cd 3d-63.

Example 2

Preparation of Hydroxy Fatty Acids

This example provides the different methods used in the preparation of Hydroxy fatty acids in the instant application, and the characterization of the resulting hydroxy fatty acids.

Preparation of Methyl oleate. Oleic acid 200.3 g (0.71 moles) and methanol 400 mL (9.88 moles) were placed into a 1 L round bottom flask equipped with a magnetic stir bar and a condenser. Concentrated sulfuric acid 1.1 mL (0.02 moles) was added dropwise and the solution was heated to reflux for 3 hours. After cooling to room temperature, 200 mL hexane was added, and the solution was transferred to a separatory funnel. The lower polar layer was drained off and the remaining hexane layer was washed 3 times; first with 100 mL of 0.5 M monobasic sodium phosphate, and then 100 mL of saturated sodium chloride in succession. The solution was dried over sodium sulfate, decanted, and then concentrated in vacuo to give 206.9 g (0.70 moles) of a nearly colorless oil 98% mass yield. $^1$H NMR ($CDCl_3$): δ5.33 (m, 1.9H, —CHCH—), δ3.65 (s, 2.9H, —$CO_2$—$CH_3$), 2.29 (t, J=7.8 Hz, 2.0H, —$CH_2CO_2$—$CH_3$), 2.0 (m, 3.8H, —$CH_2$CHCH$CH_2$—), 1.61 (m, 2.0H, —$CH_2CH_2CO_2$—), 1.36-1.19 (m, 20.5H, —$CH_2$—), 0.87 (t, J=7.2 Hz, 2.9H, —$CH_3$). $^{13}$C NMR ($CDCl_3$): δ174.1 (—$CH_2CO_2$—$CH_3$), 129.9 and 129.7 (—CHCH—), 51.3 (—$CH_2CO_2$—$CH_3$), 34.0 (—$CH_2CO_2$—$CH_3$), 31.8 (—$CH_2CH_2CH_3$) 29.7-29.0 (multiple signals, —$CH_2$—), 27.2 and 27.1 (—CH$_2$CHCHCH$_2$—), 24.9 (—CH$_2$CH$_2$CO$_2$—), 22.6 (—CH$_2$CH$_3$) and 14.0 (—CH$_3$) ppm.

Preparation of Methyl 9,10-epoxystearate. Methyl oleate 199.5 g (0.67 moles) was combined with 400 mL hexane and placed into a 1 L round bottom flask equipped with overhead mechanical stirrer. Formic acid 31.7 g (0.68 moles) and hydrogen peroxide 171.4 g (1.51 moles) were added and the reaction was stirred vigorously. After 21 hours, 22% starting material remained (GC analysis), therefore an additional aliquot of hydrogen peroxide 16.8 g (0.15 moles) was added to the reaction. After a total of 44 hours reaction time, 8% starting material remained (GC analysis) and 6.2 g (0.05 moles) of additional hydrogen peroxide was added. After 71 hours, 2.6% of starting material remained at which point the reaction was transferred to a separatory funnel and washed 3 times with 100 mL of 0.5 M monobasic sodium phosphate, followed by 100 mL of saturated sodium chloride repeatedly until the aqueous layer no longer tested positive for oxidant as determined by negative KI starch test strip. The solution was then dried over sodium sulfate, decanted from the sodium sulfate into a 1 L round bottom flask and then concentrated in vacuo to give 198.8 g (0.64 moles, 95% mass yield) of a near colorless, slightly viscous oil. $^1$H NMR (CDCl$_3$): δ3.65 (s, 2.9H, —CO$_2$—CH$_3$), 2.88 (m, 1.5H, —CH(O)CH—), 2.28 (t, J=7.5 Hz, 2.0H, —CH$_2$CO$_2$—CH$_3$), 1.61 (m, 2.3H, —CH$_2$CH$_2$CO$_2$—), 1.48 (m, 5.0H, —CH$_2$CH(O)CH—CH$_2$—), 1.41-1.21 (m, 17.9H, —CH$_2$—), 0.86 (t, J=7.3 Hz, 2.9H, —CH$_3$). $^{13}$C NMR (CDCl$_3$): δ174.2 (—CH$_2$CO$_2$—CH$_3$), 57.2 and 57.1 (—CH(O)CH—), 51.4 (—CH$_2$CO$_2$—CH$_3$), 34.0 (—CH$_2$CO$_2$—CH$_3$), 31.8 (—CH$_2$CH$_2$CH$_3$) 29.5-29.0 (multiple signals, —CH$_2$—), 27.8 and 27.7 (—CH$_2$CH(O)CH—CH$_2$—), 26.6 and 26.5 (—CH$_2$CH$_2$CH(O)CH—CH$_2$CH$_2$—), 24.9 (—CH$_2$CH$_2$CO$_2$—), 22.6 (—CH$_2$CH$_3$) and 14.0 (—CH$_3$) ppm.

Preparation of Methyl 9-hydroxystearate and methyl 10-hydroxystearate. Epoxidized methyl oleate 197.2 g (0.63 moles), oxalic acid 0.94 g (0.007 moles), 10% palladium on carbon 1.99 g (0.002 moles) were mixed with 400 mL of ethyl acetate in a 1 L stainless steel pressure reactor. The reactor was twice filled and emptied with 6895 Kpa of hydrogen gas. Then the reactor was charged with 6895 Kpa of hydrogen and heated to 50° C. with the mixture stirred continuously. After 2 hours, the reaction was cooled to room temperature and filtered to remove the palladium on carbon using a Buchner funnel under vacuum through a #50 Whatman filter paper covered with a layer of CELITE filter agent (Imerys Minerals California, Inc; Lompoc, Calif., USA) The filtered reaction mixture was placed in a separatory funnel and was washed 4 times with 100 mL 0.5 M monobasic sodium phosphate until a pH equal to 5 was achieved. The reaction mixture was then washed 2×100 mL of saturated sodium chloride solution removing the bottom brine layer after each wash. The solution was then dried over sodium sulfate, decanted into a 1 L round bottom flask and concentrated in vacuo to give 179.7 g (0.57 moles, 90.8% mass yield) of white solid, hydroxy methyl stearate. GC analysis showed 86.6% methyl 9(10)-hydroxy stearate with 5% 9(10)-keto methyl stearate as a contaminate. To further increase the purity of the hydroxy, a sodium borohydride reduction of the ketone side product was conducted. Dissolved 179.7 g (0.57 moles) of a mixture of methyl 9(10)-hydroxy stearate contaminated with 5% methyl 9(10)-keto stearate (0.03 moles) into a 360 ml of methanol in a 1 L round bottom flask equipped with a magnetic stirrer. Sodium borohydride 1.1 g (0.03 moles) was added to the reaction, a significant amount of gas evolution (foaming) was observed. After 15 minutes a clear solution was observed, and the reaction was stirred for an additional 2 hours. The reaction was transferred to a separatory funnel with 200 ml ethyl acetate and the reaction was washed 3×100 mL of 0.5 M monobasic sodium phosphate until a pH equal to 5 was achieved. The reaction was then washed twice with 100 mL of saturated sodium chloride solution. The solution was then dried over sodium sulfate, decanted and then concentrated in vacuo to give 171.4 g (0.54 moles, 95.8% mass yield) of white solid. Material was recrystallized with 1.7 L of hexane to give 142.8 g (0.46 moles, 79.8% mass yield) methyl 9(10)-hydroxy stearate that was 97% pure by GC (retention time 16.80 min). $^1$H NMR (CDCl$_3$): δ3.64 (s, 2.9H, —CO$_2$—CH$_3$), 3.54 (s, 1.0H, —CH$_2$CH(OH)—CH$_2$—), 2.27 (t, J=7.7 Hz, 2.0H, —CH$_2$CO$_2$—CH$_3$), 1.82 (s, 1.1H, O—H), 1.59 (m, 2.3H, —CH$_2$CH$_2$CO$_2$—), 1.40 (m, 6.4H, —CH$_2$CH(OH)—CH$_2$—), 1.34-1.16 (m, 20.5H, —CH$_2$—), 0.87 (t, J=7.2 Hz, 3.1H, —CH$_3$). $^{13}$C NMR (CDCl$_3$): δ174.2 (2 signals, —CH$_2$CO$_2$—CH$_3$), 71.9 and 71.8 (—CH$_2$CH(OH)—CH$_2$—), 51.4 (—CH$_2$CO$_2$—CH$_3$), 37.5, 37.4 and 37.4 (—CH$_2$CH(OH)—CH$_2$—), 34.0 (2 signals, —CH$_2$CO$_2$—CH$_3$), 31.9 (—CH$_2$CH$_2$CH$_3$), 29.7-25.5 (multiple signals, —CH$_2$—), 24.9 (2 signals —CH$_2$CH$_2$CO$_2$—), 22.6 (—CH$_2$CH$_3$) 14.0 (—CH$_3$).

Preparation of Methyl 9-hydroxy, 10-acetyl stearate and methyl 9-acetyl, 10-hydroxy stearate. Epoxidized methyl oleate 50.0 g (0.16 mol), acetic acid 9.61 g (0.16 mol), and 10% palladium on carbon 0.51 g (0.0005 mol) were placed in a 100 mL stainless steel pressure reactor. The reactor was twice filled with 1103 Kpa of hydrogen gas and then emptied. The reactor was charged with 1103 Kpa of hydrogen and heated to 120° C. with continuous stirring. After 2 hours, the reaction was cooled to room temperature and an aliquot was removed, diluted with ethyl acetate, filtered through a silica plug, washed twice with 0.5 M monobasic sodium phosphate, dried over sodium sulfate and then injected in the GC. GC analysis showed 27.6% of starting material remaining and 46.2% of hydroxy acetate. GC/MS-CI with methane showed a M−1 peak of 371 m/z and M+29 peak of 401 m/z which is indicative of a ring opened hydroxy acetate ester product (MW 372 g/mol).

Example 3

Product Characterization

Methyl oleate was epoxidized to 9,10-epoxy stearate using a peracetic hydrogen peroxide epoxidation method (Findley T. W. et al., 1945 Supra) and this epoxide was used as the starting material for all subsequent hydrogenation studies. Below in Table 1, are provided the reaction conditions used in these studies, and the products formed.

TABLE 1

CONDITIONS AND PRODUCTS

| Entry | H+ Cat. | H+ equiv | Pd equiv | H₂ (psi) | Temp (° C.) | Time (h) | % SM | % Hydroxy | % Ketone | % C18:0 |
|---|---|---|---|---|---|---|---|---|---|---|
| 1 | Acetic | 161.04 | 0.0053 | ATM | R.T. | 2 | 82.2 | 4.0 | 0.0 | 5.0 |
| 2 | Acetic | 1.0 | 0.0069 | 160 | 120 | 5 | 2.6 | 79.8 | 10.3 | 0.0 |
| 3 | Acetic | 1.0 | 0.0064 | 160 | 100 | 11 | 0.0 | 82.4 | 9.6 | 0.0 |
| 4 | Acetic | 1.0 | 0.0030 | 160 | 120 | 2 | 27.6 | 0.0 | 0.0 | 0.0 |
| 5 | Oxalic | 1.0 | 0.0059 | 160 | 120 | 1 | 0.0 | 55.0 | 17.1 | 19.0 |
| 6 | Oxalic | 1.0 | 0.0059 | 160 | 80 | 2 | 0.0 | 70.8 | 8.3 | 21.0 |
| 7 | Oxalic | 1.0 | 0.0059 | 160 | R.T. | 4 | 0.0 | 69.6 | 6.7 | 22.0 |
| 8 | Oxalic | 0.01 | 0.0077 | 160 | R.T. | 6 | 0.0 | 83.4 | 6.3 | 8.0 |
| 9 | Oxalic | 0.01 | 0.0059 | 1000 | 50 | 1.5 | 0.0 | 86.9 | 5.6 | 6.0 |
| 10 | Oxalic | 0.01 | 0.0030 | 1000 | 50 | 2 | 1.3 | 86.6 | 5.0 | 6.0 |
| 11 | None | None | 0.0059 | 160 | 120 | 11.5 | 0.0 | 78.1 | 13.8 | 5.7 |

All reactions were run in ethyl acetate as the solvent and 10% Pd/C as a catalyst except entry 1 where acetic acid served as the solvent, and entry 4 which had no solvent. The reaction of entry 4 produced 72.4% methyl 9(10)-hydroxy 9(10)-acetyl stearate.

Figure 1A:
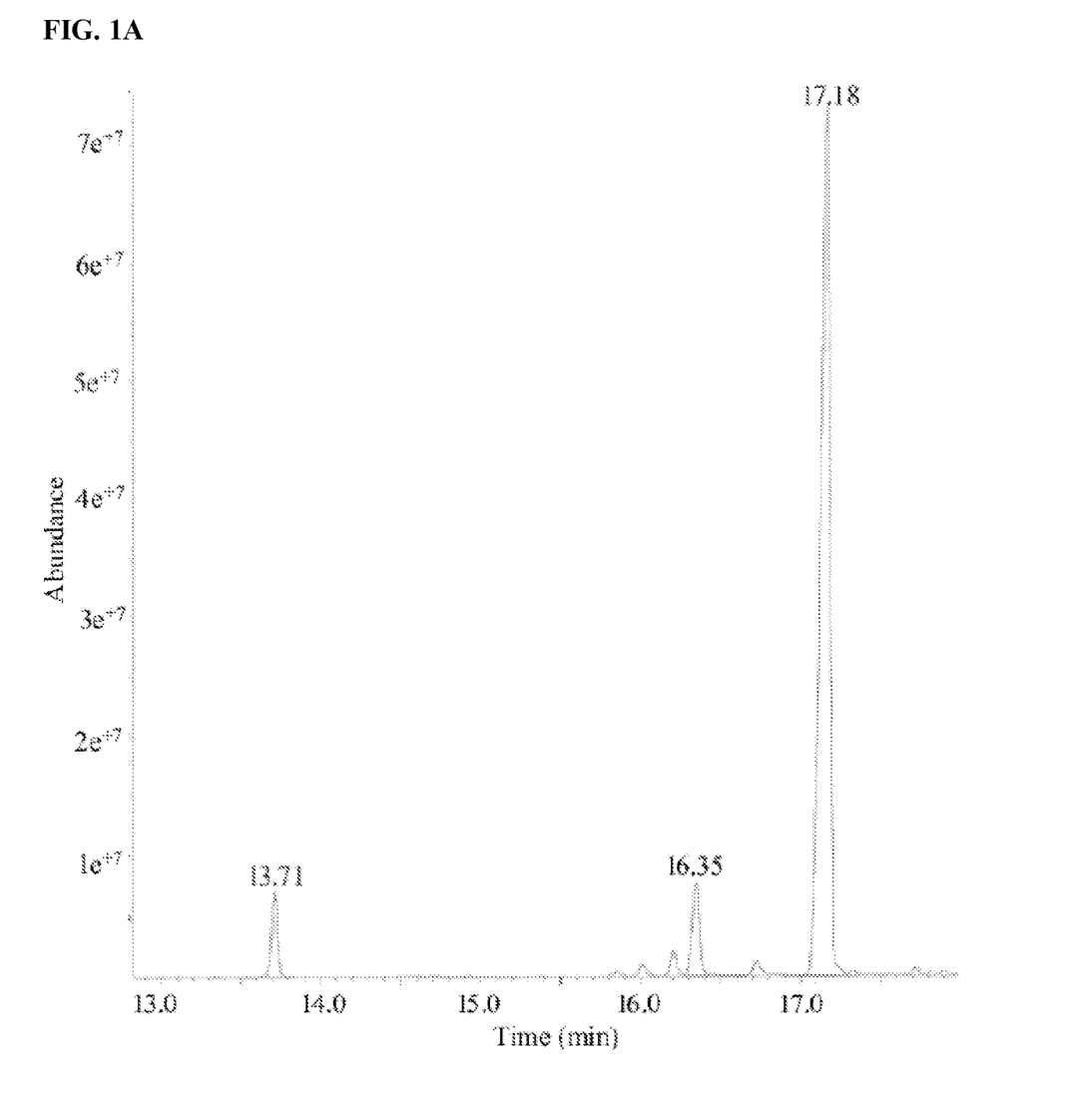
FIG. 1A and FIG. 1B depict graphs of the Gas Chromatography Mass Spectrum obtained for the Hydroxy products as their Trimethylsilyl (TMS) ether derivatives. The trace on FIG. 1A identifies hydroxyl as the major product, and saturates and ketone as minor products. The trace on FIG. 1B shows the peaks indicative of the cleavage on both sides of the TMS functionality with the alkyl fragment at the 9-position of 229, and the 10-position fragment of 215.
Figure 1B:
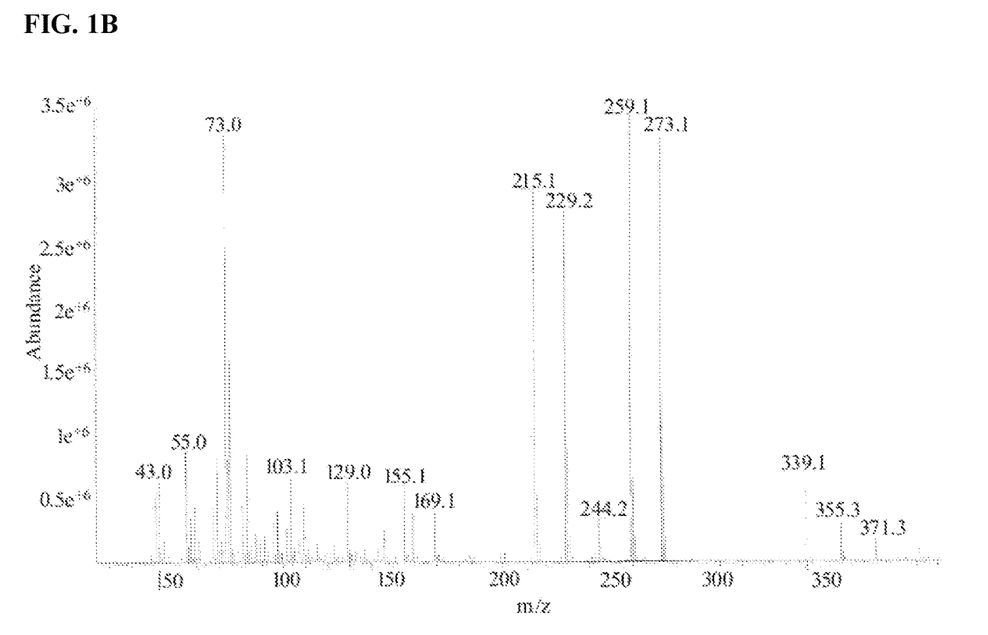
Figure 1C:
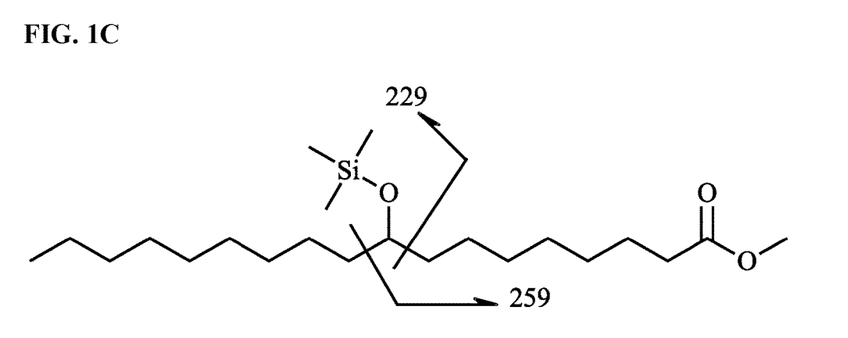
FIG. 1C presents the carboxylic chain with the cleavage sites at both sides of the TMS functionality indicated.

All the reaction products were characterized by GCMS and NMR ($^1$H, $^{13}$C, DEPT, HSQC, HMBC and COSY), as stated above. A GC with FID detector was used to quantitate reaction product distribution from the hydrogenation studies. Furthermore, GCMS analysis of the hydroxy products as their Trimethylsilyl (TMS) ether derivate was used to characterize the positional isomers produced from the hydrogenation reactions. As seen in FIG. 1, equal amounts of ion cleavage products associated with the hydroxyl located at both the 9 and 10 position along the chain were observed in the EI mass spectrum. As seen in FIG. 1B, the key fragments resulting from cleavage on both sides of the TMS functionality with the alkyl side fragment at the 9-position of 229 and the 10-position fragment of 215 were detected. The associated carboxylic chain fragment of 259 for the 9-position and 273 for the 10-position were also observed. TMS+ at 73 is a prominent peak since this stable ion is so readily lost, a M+ peak was not observed, however an M−15 (loss of methyl) at 371 was observed. The mass spectrum also confirmed the identity of the saturated stearate with M+ of 298 and the 9-keto and 10-keto stearate with M+ of 312. The ketone was confirmed by alpha cleavage of the carbonyl to yield molecular ion 199 m/z for the 9 position and 213 m/z for the 10 position. FIG. 1C depicts the structure of the TMS derivative indicating the alkyl side fragment at the 9-position of 229 and the 10-position fragment of 215.

Figure 2:
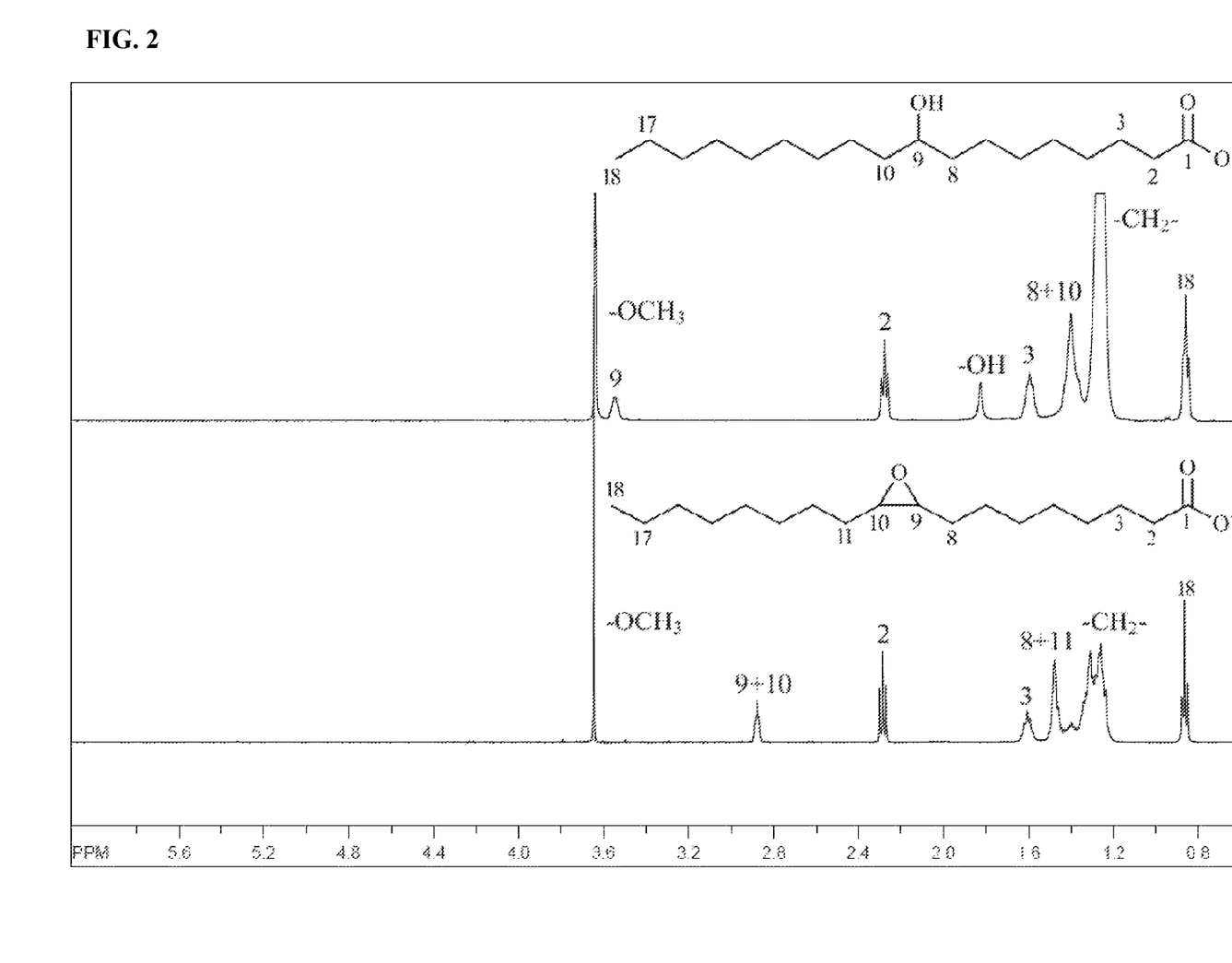
FIG. 2 depicts an NMR stack of epoxidized and hydroxy methyl stearate. The top portion of the figure shows the hydroxy methyl stearate chemical structure and an NMR spectrum obtained for hydroxy methyl stearate. The bottom portion of the figure shows the epoxidized methyl stearate chemical structure and an NMR spectrum obtained for epoxidized methyl stearate.
Figure 3A:
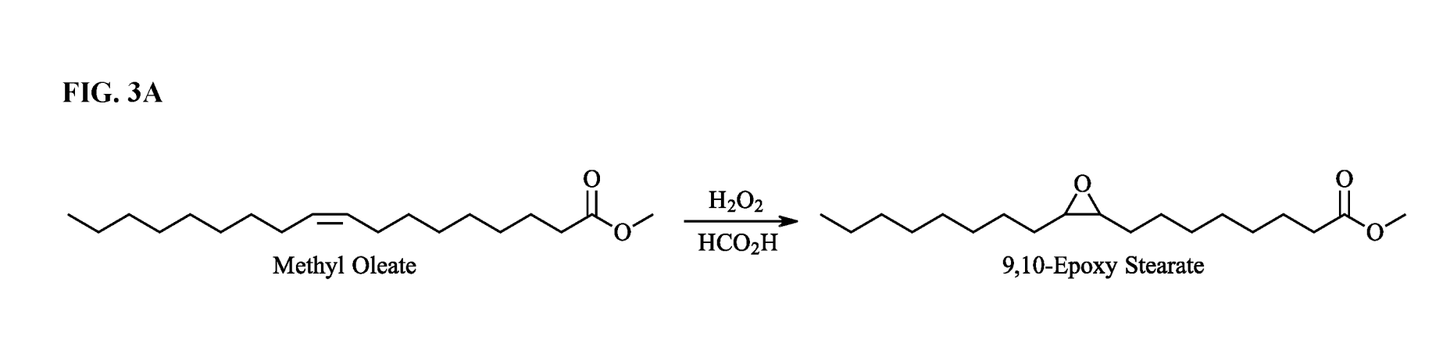
FIG. 3A depicts a reaction scheme for the treatment of methyl oleate with formic acid and hydrogen peroxide.
Figure 3B:
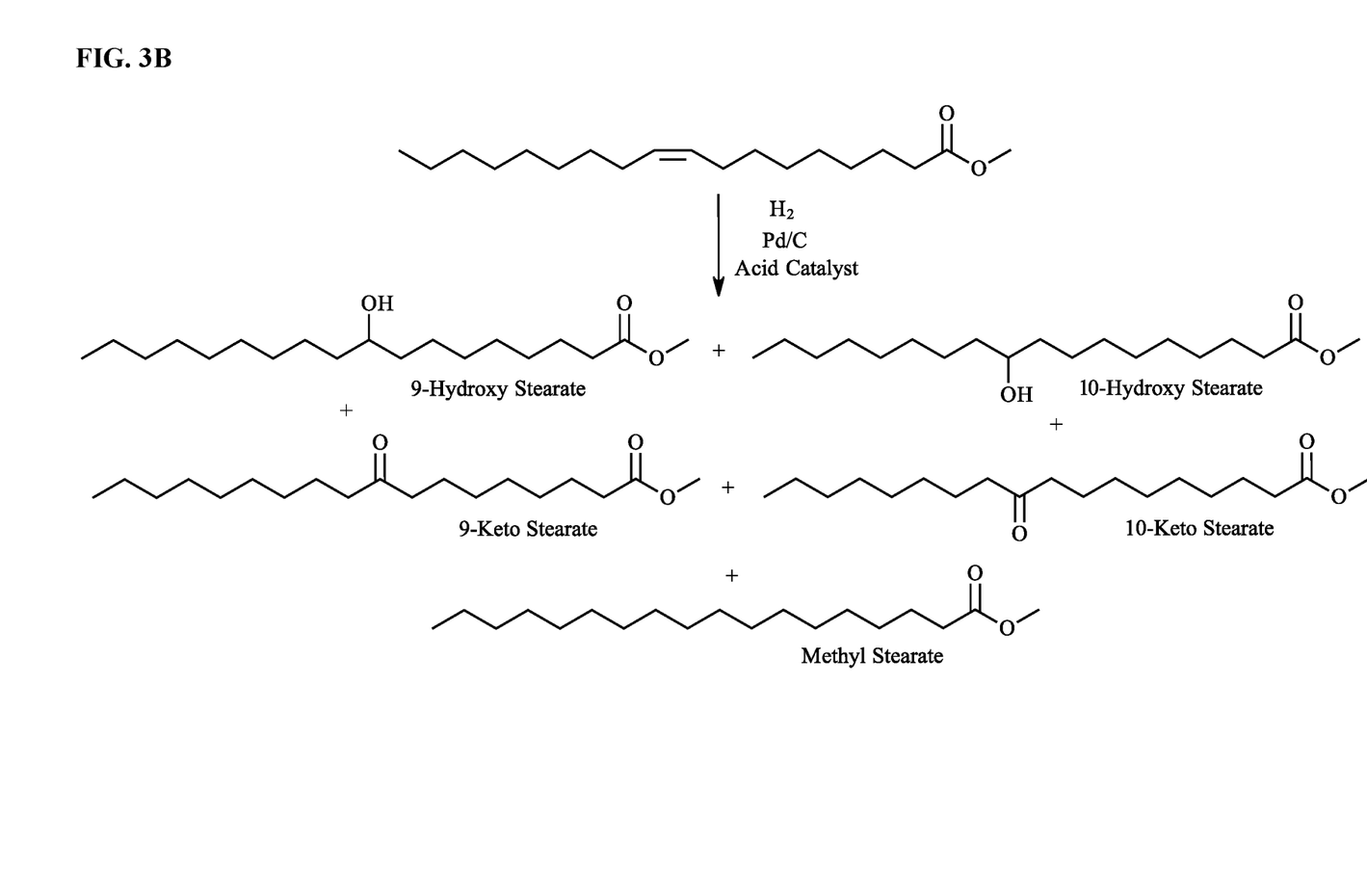
FIG. 3B depicts a reaction scheme for the treatment of methyl oleate with acid palladium on carbon.
Figure 3C:
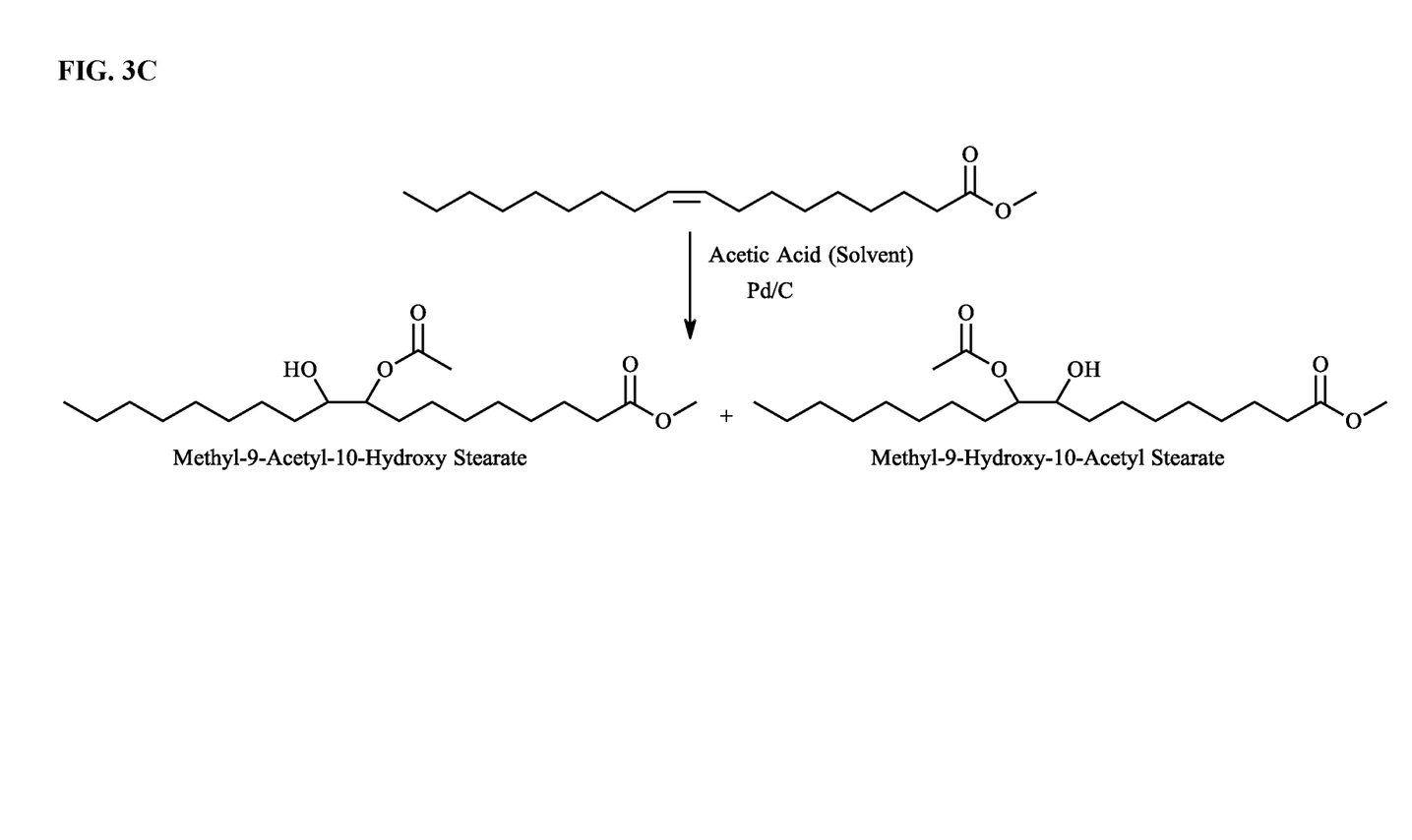
FIG. 3C depicts a reaction scheme for the treatment of methyl oleate with glacial acetic acid as the solvent.

The NMR stack of the epoxidized and hydroxy methyl stearate is shown in FIG. 2. The NMR analysis indicated a new resonance of 3.55 ppm for the methine attached to the hydroxyl functionality, and the concurrent disappearance of the signal for the epoxide hydrogens at 2.88 ppm. The $^{13}$CNMR had new resonances at 71.8 and 71.9 for the hydroxyl methine carbon, which were associated with the disappearance of the epoxide methine carbons at 57.1 and 57.2 ppm. The literature reports (Mack C. H. and Bickford W. G., 1953, Supra) the successful hydrogenation of oleic acid with a 10% Pd/C metal catalyst using glacial acetic acid as both solvent and hydrogen ion co-catalyst under 2 atmospheres of hydrogen pressure. Unfortunately, the absence of modern spectroscopic instrumentation such as NMR and Mass spectrometry limited their ability to characterize the products accurately. Both 9-hydroxy and 10-hydroxy isomers, as well as ketones were later identified (Cochrane C. C. and Harwood H Y. J., 1961, supra) as products from this reaction. Furthermore, Mack C. H. and Bickford W. G. (1953, Supra) reported the formation of hydroxy acetates from ring opening and addition of the epoxide by the acetic acid. Entry 1 from Table 1 was a reaction run under atmospheric pressure where hydrogen gas was bubbled through an open reaction mixture, glacial acetic acid was used as the acid catalyst and solvent, with 0.5 mole % of Pd/C used as the supported metal catalyst. Under these reaction conditions, only 4% reduction to the hydroxy fatty acids was observed. A possible scheme for the reaction is shown in FIG. 3C. However, as seen on Entry 2 from Table 1, when using 1.0 mole equivalent of acetic acid, and a hydrogen pressure of 160 psi under the same metal catalyst equivalents, after 5 hours at 120° C. 79.8% hydroxy fatty acids were observed with 10.3% formation of ketone side products. Entry 3 from Table 1 shows that when the temperature was decreased to 100° C., and the reaction time increased to 11 hours, the result was 82.4% hydroxy fatty acid with nearly identical ketone formation (9.6%) as Entry 1. The formation of hydroxy acetate esters of the stearate (72.4%) was also observed in Entry 4, Table 1 when 1.0 equivalent of acetic acid was used as the acid catalyst with no solvent present, and a temperature of 120° C. This demonstrated the potential for the acid catalyst to open the epoxide and form the acetate addition product by forming a "carbocation" like transition state. Clearly a full carbocation did not occur since migration of the olefin or the hydroxy position did not occur which would happen if it were a full carbocation. Not intending to be bound by theory, it may be that in the reaction mechanism the weak organic acid proton polarizes the epoxide C—O bond without developing a full carbocation. Mack and Bickford (1953, supra) attempted the reaction in the presence of sulfuric acid but found addition products by the conjugate sulfonate base to the molecule as a result of establishing a discrete carbocation under those reaction conditions. Therefore, choice of an acid that can polarize the epoxide bond without generating a discrete carbocation was desirable. Within the simple organic acids, it was postulated that the strongest unsubstituted organic acid, oxalic, with a pKa of 1.25, compared to acetic with a pKa 4.74, would provide faster rates of hydrogenation without generating a carbocation and the side products associated with that formation. Entries 5-9 of Table 1 report the results of hydrogenation reactions with oxalic acid as a co-catalyst. In entry 5 of Table 1, oxalic at 1.0 mole equivalent to the epoxide had complete hydrogenation of the epoxide in 1 hour at 120° C., but significant dehydrogenation to the ketone (17.1%), with only 55% hydroxy remaining, and saturates also increased to 19.0%. Entries 5-7 of Table 1 demonstrate that as temperature increased saturates and ketones were formed at faster rates. Entries 7 and 8 indicate that by reducing the amount of oxalic acid catalyst the rate of saturate formation was greatly reduced (5.7% of which 4.4% is present in the starting material) yet hydroxy yield remained good at 83.4%. By increasing the temperature slightly to 50° C., from room temperature in entry 9 compared to entry 8, the rate for the hydrogenation was reduced from 6 hours to 1.5 hours. In addition, the conversion to ketones (5.6%) was reduced, and a good yield (86.9%) of hydroxy product was observed. When the Pd/C catalyst concentration was cut in half to 0.3 mole % from 0.6 mole % no effect was observed on the rate of hydrogenation or on the product distribution, Entry 9 versus 10. The control reaction, entry 11 where no acid catalyst was added, showed significant (13.8%) formation of ketones, and the reaction required 11.5 hours to consume all of the starting material. Of particular note for Entry 11, the reaction where no acid catalyst is present, formation of saturates did not substantially occur (5.7%) and remained nearly at the level as those present in the starting material. This reaction supports a mechanism for the formation of saturates arising in which a hydrolysis reaction of the alcohol occurs possibly via its protonated ester (acetate or oxalate) to yield an olefin that is subsequently hydrogenated over the Pd/C catalyst.

Finally, the yield of hydroxy ester may be further maximized by reduction of the ketone by-products with $NaBH_4$ in an equal molar ratio of ketone to hydride over a 2-hour reaction at room temperature. This provided a crude product containing greater than 92% hydroxy ester and no ketones. Crystallization of this material gave an 80% mass recovery of a hydroxy ester with a purity greater than 97%.

We claim:

1. A method for the synthesis of at least one mono hydroxy fatty acid, the method comprising reacting in a pressurized container at least one epoxidized fatty acid or epoxidized fatty acid ester in a solvent, with an organic acid and a palladium or platinum catalyst in a hydrogen atmosphere to obtain at least one mono hydroxy fatty acid.

2. The method of claim 1, wherein the at least one epoxidized fatty acid is obtained from sunflower, safflower, tallow, pennycress, *crambe*, rapeseed, *Brassica carinata*, meadowfoam, coriander, soybean, camelina, or jojoba.

3. The method of claim 1, wherein the organic acid is acetic acid, oxalic acid, trifluoroacetic acid, trichloroacetic acid, or tribromoacetic acid.

4. The method of claim 3, wherein the organic acid is oxalic acid.

5. The method of claim 1, wherein the catalyst is palladium on carbon or platinum on carbon.

6. The method of claim 5, wherein the catalyst is palladium on carbon.

7. The method of claim 6, wherein 1 equivalent of the epoxidized fatty acid is reacted with from about 0.0020 equivalents of palladium to about 0.021 equivalents of palladium.

8. The method of claim 1, wherein the pressure is at least about 14 psi to at least about 1100 psi.

9. The method of claim 1, wherein the pressure is at least about 160 psi Hydrogen to at least about 1000 psi hydrogen.

10. The method of claim 1, wherein the method produces at least one hydroxy fatty acid and at least one ketone fatty acid.

11. The method of claim 10, wherein less than about 18% of the reaction product is ketone fatty acid.

12. The method of claim 1, wherein the solvent is not n-butyl propionate containing 1% sulfuric acid; ethanol; petroleum ether containing 1% acetic acid; anhydrous propionic acid; or glacial acetic acid.

13. The method of claim 1, wherein the solvent is ethyl acetate.

14. The method of claim 1, wherein the at least one epoxidized fatty acid has more than 7 carbons.

15. The method of claim 1, wherein the temperature is from about 20° C. to about 180° C.

16. The method of claim 1, wherein no acetate esters are synthesized.

17. The method of claim 1, wherein the at least one epoxidized fatty acid is epoxidized methyl oleate, and the hydroxy fatty acid obtained is a 50:50 mixture of methyl 9-hydroxystearate and methyl 10-hydroxystearate.

18. The method of claim 1, wherein the method further comprises obtaining the epoxidized fatty acid by reacting an unsaturated fat with formic acid and hydrogen peroxide at room temperature and pressure.

* * * * *